(12) United States Patent
Mishra et al.

(10) Patent No.: US 9,227,061 B2
(45) Date of Patent: Jan. 5, 2016

(54) BILATERAL AUDITORY PROSTHESIS SYSTEMS AND METHODS

(75) Inventors: Lakshmi N. Mishra, Valencia, CA (US); Lee F. Hartley, Valencia, CA (US)

(73) Assignee: Advanced Bionics AG, Staefa (CH)

(*) Notice: Subject to any disclaimer, the term of this patent is extended or adjusted under 35 U.S.C. 154(b) by 3 days.

(21) Appl. No.: 14/237,806

(22) PCT Filed: Aug. 10, 2011

(86) PCT No.: PCT/US2011/047212
§ 371 (c)(1),
(2), (4) Date: Feb. 7, 2014

(87) PCT Pub. No.: WO2013/022444
PCT Pub. Date: Feb. 14, 2013

(65) Prior Publication Data
US 2014/0188189 A1    Jul. 3, 2014

(51) Int. Cl.
- *A61N 1/00* (2006.01)
- *A61N 1/36* (2006.01)
- *A61N 1/372* (2006.01)
- *A61N 1/375* (2006.01)

(52) U.S. Cl.
CPC .............. *A61N 1/36032* (2013.01); *A61N 1/375* (2013.01); *A61N 1/37217* (2013.01); *A61N 1/37288* (2013.01)

(58) Field of Classification Search
CPC .................................................. A61N 1/36032
USPC ........................................... 607/2, 56, 57, 60
See application file for complete search history.

(56) References Cited

U.S. PATENT DOCUMENTS

| | | | |
|---|---|---|---|
| 2003/0036782 A1* | 2/2003 | Hartley et al. | 607/57 |
| 2009/0030484 A1* | 1/2009 | Chambers | 607/57 |
| 2009/0067653 A1 | 3/2009 | Meskens et al. | |

FOREIGN PATENT DOCUMENTS

WO    WO-2007/090243    8/2007

OTHER PUBLICATIONS

International Search Report and Written Opinion received in International Application No. PCT/US11/047212, dated Sep. 20, 2012.

* cited by examiner

*Primary Examiner* — Theodore Stigell
*Assistant Examiner* — Nadia A Mahmood
(74) *Attorney, Agent, or Firm* — ALG Intellectual Property, LLC (57) ABSTRACT

An exemplary bilateral auditory prosthesis system includes 1) a primary auditory prosthesis configured to be implanted on a first side of a head of a patient, 2) a secondary auditory prosthesis configured to be implanted on a second side of the head of the patient and to be communicatively coupled to the primary auditory prosthesis with one or more wires, the second side being contralateral to the first side, and 3) a sound processor configured to be communicatively coupled to the primary auditory prosthesis and to control an operation of the secondary auditory prosthesis by transmitting control data to the secondary auditory prosthesis by way of the primary auditory prosthesis and at least one wire included in the one or more wires. Corresponding systems and methods are also disclosed.

20 Claims, 10 Drawing Sheets

BILATERAL AUDITORY PROSTHESIS SYSTEMS AND METHODS

BACKGROUND INFORMATION

Bilateral auditory prosthesis systems (i.e., auditory prosthesis systems that provide electrical stimulation to both ears of a patient) offer many advantages in terms of performance over conventional auditory prosthesis systems that are capable of only providing electrical stimulation to one of the patient's ears. For example, by applying electrical stimulation to both ears of a patient instead of one, bilateral auditory prosthesis systems (e.g., bilateral cochlear implant systems) are capable of providing a more realistic representation of audio content to the patient.

Unfortunately, however, bilateral auditory prosthesis systems typically require two externally worn sound processors—one for each ear. This makes bilateral auditory prosthesis systems costly to implement and maintain. Dual sound processors are also cumbersome, bulky, and aesthetically unpleasing for many patients.

One attempted solution to this problem has been to connect two electrode arrays (or "electrode leads") to a single auditory prosthesis that is implanted on a particular side (e.g., the right side) of a patient's head. One of the electrode arrays may be implanted on the same side as the auditory prosthesis and the other may be implanted on a contralateral side (e.g., the left side) of the patient's head in order to facilitate bilateral electrical stimulation of sites located within both ears of the patient. A single sound processor may then be used to direct the auditory prosthesis to apply electrical stimulation to both ears.

A particular problem with this approach is that the electrode array configured to be implanted on the contralateral side has to be tunneled from the implant site of the auditory prosthesis all the way across the patient's head in order to reach its intended destination. Because the electrode array may include sixteen or more electrodes, a relatively large number (e.g., sixteen or more) of corresponding wires have to be tunneled across the head in this manner. Tunneling a large number of wires across the head can be difficult, dangerous, unreliable, and costly. Moreover, such a large number of wires may begin to bulge and/or otherwise bother the patient over the course of time. Finally, if the electrode array ever needs to be replaced in the future, a whole other set of wires will again have to be tunneled across the patient's head.

SUMMARY

An exemplary bilateral auditory prosthesis system includes 1) a primary auditory prosthesis configured to be implanted on a first side of a head of a patient, 2) a secondary auditory prosthesis configured to be implanted on a second side of the head of the patient and to be communicatively coupled to the primary auditory prosthesis with one or more wires, the second side being contralateral to the first side, and 3) a sound processor configured to be communicatively coupled to the primary auditory prosthesis and to control an operation of the secondary auditory prosthesis by transmitting control data to the secondary auditory prosthesis by way of the primary auditory prosthesis and at least one wire included in the one or more wires.

An exemplary auditory prosthesis includes a communication facility configured to receive control data from a sound processor and a processing facility configured to 1) determine that the control data is configured to control an operation of a secondary auditory prosthesis communicatively coupled to the auditory prosthesis with one or more wires, and 2) transmit, in response to the determination, the control data to the secondary auditory prosthesis by way of at least one wire included in the one or more wires.

An exemplary method includes a primary auditory prosthesis device 1) receiving control data from a sound processor, 2) determining that the control data is configured to control an operation of a secondary auditory prosthesis communicatively coupled to the primary auditory prosthesis with one or more wires, and 3) transmitting, in response to the determination, the control data to the secondary auditory prosthesis by way of at least one wire included in the one or more wires.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 2A-2C show various configurations wherein one or more wires connect a secondary auditory prosthesis to a primary auditory prosthesis according to principles described herein.

DETAILED DESCRIPTION

Bilateral auditory prosthesis systems that utilize a single sound processor and that minimize the number of wires that are tunneled across a patient's head are described herein. For example, an exemplary bilateral auditory prosthesis system includes a primary auditory prosthesis (e.g., a primary cochlear implant) configured to be implanted on a first side of a head of a patient, a secondary auditory prosthesis (e.g., a secondary cochlear implant) configured to be implanted on a second contralateral side of the head of the patient and to be communicatively coupled to the primary auditory prosthesis with one or more wires, and a single sound processor configured to be communicatively coupled to the primary auditory prosthesis. In this configuration, the sound processor may control an operation of either auditory prosthesis.

For example, the sound processor may control an operation of the primary auditory prosthesis (e.g., direct the primary auditory prosthesis to generate and apply electrical stimulation representative of an audio signal to one or more stimulation sites within a cochlea located on the first side of the patient's head) by transmitting control data intended for the primary auditory prosthesis to the primary auditory prosthesis. Additionally or alternatively, the sound processor may control an operation of the secondary auditory prosthesis (e.g., direct the secondary auditory prosthesis to generate and apply electrical stimulation representative of an audio signal to one or more stimulation sites within a cochlea located on the second contralateral side of the patient's head) by transmitting control data to the secondary auditory prosthesis by way of the primary auditory prosthesis and at least one wire included in the one or more wires. As will be described below, the sound processor may also provide power to either auditory prosthesis in a similar manner.

Many advantages are associated with the bilateral auditory prosthesis systems described herein. For example, the use of a secondary auditory prosthesis obviates the need for an electrode array to be tunneled across the patient's head. Instead, the electrode array may be connected directly to the secondary auditory prosthesis. This makes future replacement of the electrode array a relatively simple procedure.

Moreover, communication between the sound processor and the secondary auditory prosthesis may be facilitated using a relatively low number of wires (e.g., four or fewer wires) connecting the primary and secondary auditory prostheses. For example, as will be described below, control data and one or more power signals may be transmitted by the sound processor to the secondary auditory prosthesis by way of a single wire that connects the primary and secondary auditory prostheses. While the one or more wires that connect the secondary auditory prosthesis to the primary auditory prosthesis may still need to be tunneled across the patient's head, such a procedure may be relatively less invasive because of the relatively fewer wires that are involved (e.g., four or fewer versus sixteen or more).

Figure 1:
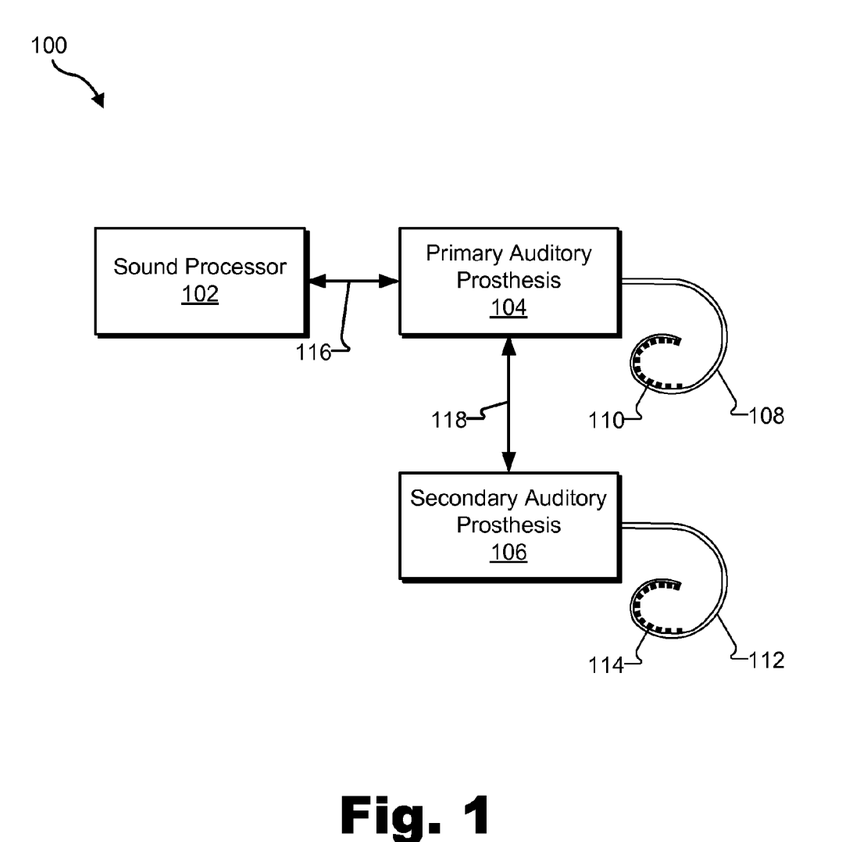
FIG. 1 illustrates an exemplary bilateral auditory prosthesis system according to principles described herein.

FIG. 1 illustrates an exemplary bilateral auditory prosthesis system 100 (or simply "system 100"). As shown, system 100 may include a sound processor 102, a primary auditory prosthesis 104, and a secondary auditory prosthesis 106. Primary auditory prosthesis 104 may be communicatively coupled to a first electrode lead 108 having a plurality of electrodes 110 disposed thereon and secondary auditory prosthesis 106 may be communicatively coupled to a second electrode lead 112 having a plurality of electrodes 114 disposed thereon. Each of the components shown in FIG. 1 will now be described in more detail.

Sound processor 102 may include any suitable device configured to process audio content presented to an auditory prosthesis patient and/or control an operation of primary and secondary auditory prostheses 104 and 106. In some examples, sound processor 102 is implemented by an externally worn unit (e.g., a behind-the-ear device, a body worn device, etc.). Alternatively, sound processor 102 may be configured to be at least partially implanted within the patient. Various components and features of sound processor 102 will be described below.

Primary and secondary auditory prostheses 104 and 106 may each include any type of implantable stimulator (e.g., cochlear implant, brainstem implant, etc.) that may be used in association with the systems and methods described herein. In some examples, primary and secondary auditory prostheses 104 and 106 may be configured to be implanted on opposite sides of a patient's head in order to apply electrical stimulation representative of one or more audio signals by way of one or more of electrodes 110 and 114, respectively, to one or more stimulation sites associated with the auditory pathways (e.g., the auditory nerves) of the patient. For example, primary auditory prosthesis 104 may be implanted on a right side of a patient's head in order to provide electrical stimulation to one or more stimulation sites within the patient's right cochlea. Likewise, secondary auditory prosthesis 104 may be implanted on a left side of the patient's head in order to provide electrical stimulation to one or more stimulation sites within the patient's left cochlea.

As will be described below, auditory prostheses 104 and 106 may operate (e.g., generate and apply electrical stimulation by way of one or more electrodes to one or more stimulation sites within a patient) in accordance with control data provided thereto by sound processor 102. To this end, sound processor 102 may be communicatively coupled to primary auditory prosthesis 104 by way of a communication link 116 and primary auditory prosthesis 104 may be communicatively coupled to secondary auditory prosthesis 106 by way of communication link 118. Communication link 116 may be implemented by any suitable wireless or wired link as may serve a particular implementation. For example, as will be illustrated below, in configurations wherein sound processor 102 is an externally located unit, communication link 116 may be implemented by a wireless communication link.

Figure 2A:
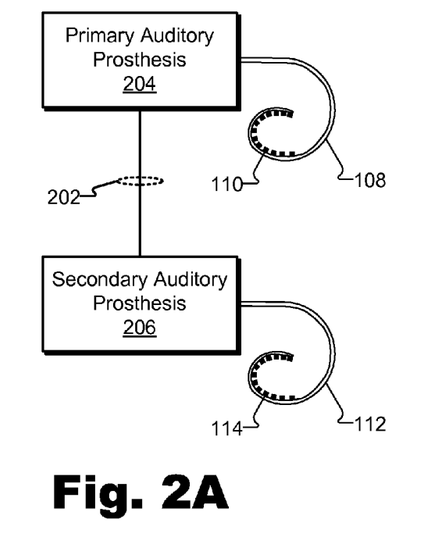
Figure 2C:
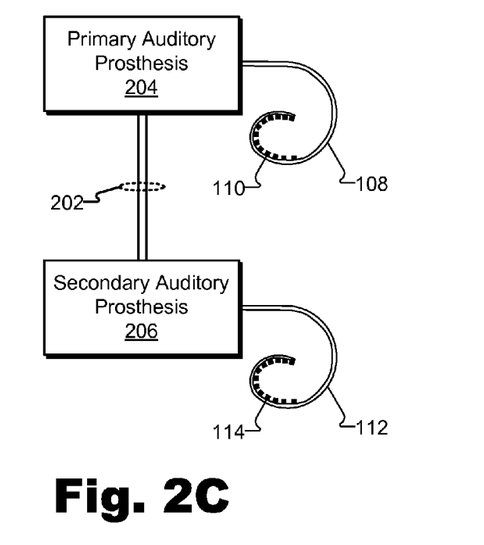

Communication link 118 may be implemented by one or more wires. For example, FIGS. 2A-2C show various configurations of system 100 in which communication link 118 is implemented by a single wire 202 (FIG. 2A), two wires 202 (FIG. 2B), and four wires 202 (FIG. 2C). It will be recognized that any other number of wires may be used to implement communication link 118. In some examples, wires 202 may be disposed within one or more cables and/or leads that may be tunneled across the head of a patient. Alternatively, each wire may be tunneled across the head individually.

In some examples, redundancy may be built into wires 202. In this manner, failure (e.g., breakage) of one or more wires may not inhibit communication between auditory prostheses 104 and 106. To illustrate, the wires 202 shown in FIG. 2C may include a first set of two wires 202 and a second set of two wires 202 that are redundant to the first set of two wires 202. Data may be normally transmitted by way of the first set of wires 202 until sound processor 102 and/or auditory prostheses 104 and 106 detect a problem with either wire included in the first set, after which data may be transmitted by way of the redundant second set of wires 202.

Figure 3:
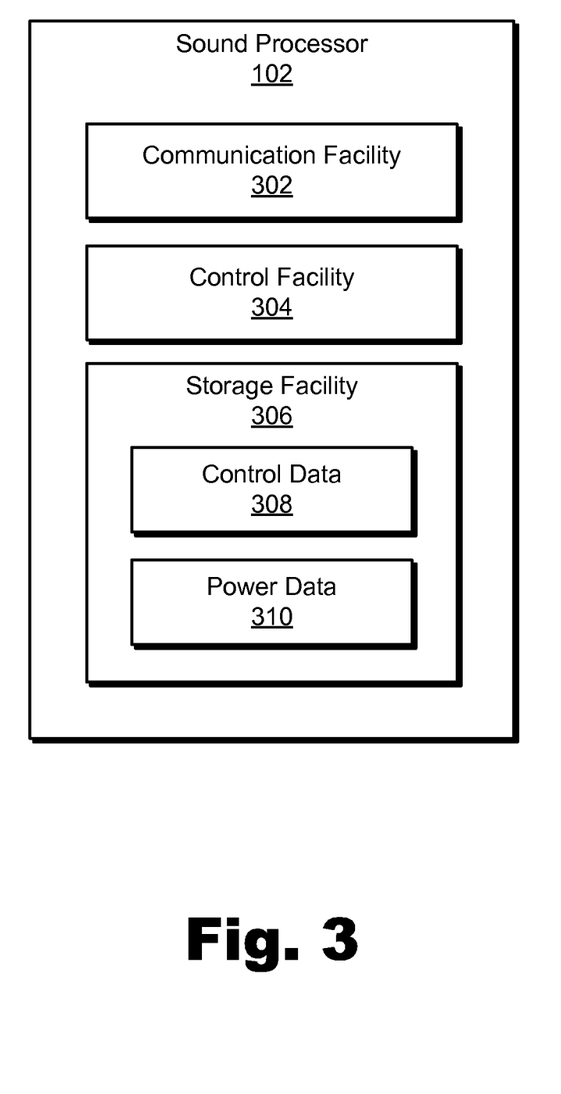
FIG. 3 illustrates exemplary components of a sound processor according to principles described herein.

FIG. 3 illustrates exemplary components of sound processor 102. As shown in FIG. 3, sound processor 102 may include a communication facility 302, a control facility 304, and a storage facility 306, which may be in communication with one another using any suitable communication technologies. Each of these facilities may include any combination of hardware, software, and/or firmware as may serve a particular application. For example, one or more of facilities 302-306 may include a computing device or processor configured to perform one or more of the functions described herein. Facilities 302-306 will now be described in more detail.

Communication facility 302 may be configured to facilitate communication between sound processor 102 and auditory prostheses 104 and 106. For example, communication facility 302 may include one or more components configured transmit control data (e.g., one or more stimulation parameters configured to direct an auditory prosthesis to generate and apply electrical stimulation representative of one or more audio signals) to primary auditory prosthesis 104 and/or to secondary auditory prosthesis 106. Communication facility 302 may be further configured to receive data (e.g., back telemetry data) from primary auditory prosthesis 104 and/or to secondary auditory prosthesis 106.

Control facility 304 may be configured to control an operation of auditory prostheses 104 and 106. For example, control facility 304 may control primary auditory prosthesis 104 by transmitting (i.e., directing communication facility 302 to transmit) control data (e.g., data representative of one or more stimulation parameters) directly to primary auditory prosthesis 104 (e.g., by way of communication link 116). Primary auditory prosthesis 106 may process the received control data and perform one or more operations (e.g., generate and apply electrical stimulation) accordingly.

Likewise, control facility 304 may control secondary auditory prosthesis 106 by transmitting control data (e.g., data representative of one or more stimulation parameters) to secondary auditory prosthesis 106 by way of primary auditory prosthesis 104 and one or more wires (e.g., one or more of wires 202) that connect secondary auditory prosthesis 106 to primary auditory prosthesis 104. To illustrate, control facility 304 may transmit control data intended for secondary auditory prosthesis 106 to primary auditory prosthesis 104. The control data may include instructions that direct primary auditory prosthesis 104 to transmit the control data to secondary auditory prosthesis 106 by way of one or more wires included in wires 202. Control facility 304 may alternatively direct primary auditory prosthesis 104 to transmit the control data to secondary auditory prosthesis 106 in any other suitable manner.

In some examples, control facility 304 may be further configured to provide power to auditory prostheses 104 and/or 106. For example, control facility 304 provide power to primary auditory prosthesis 104 by transmitting one or more power signals directly to primary auditory prosthesis 104 (e.g., by way of communication link 116). Primary auditory prosthesis 104 may then extract or otherwise derive power from the one or more power signals.

Likewise, control facility 304 may provide power to secondary auditory prosthesis 106 by transmitting one or more power signals to secondary auditory prosthesis 106 by way of primary auditory prosthesis 104 and one or more wires (e.g., one or more of wires 202) that connect secondary auditory prosthesis 106 to primary auditory prosthesis 104. To illustrate, control facility 304 may transmit one or more power signals intended for secondary auditory prosthesis 106 to primary auditory prosthesis 104 and then direct primary auditory prosthesis 104 to transmit the one or more power signals to secondary auditory prosthesis 106 by way of one or more wires included in wires 202.

Control facility 304 may transmit control data and one or more power signals to secondary auditory prosthesis 106 by way of any number of wires and/or in any suitable manner (e.g., concurrently) as may serve a particular implementation. For example, control facility 304 may transmit control data and one or more power signals to secondary auditory prosthesis 106 by way of a single wire (e.g., the single wire 202 shown in FIG. 2A or one of the wires 202 shown in FIGS. 2B and 2C). To this end, control facility 304 (and/or primary auditory prosthesis 104) may use a charge balanced data encoding scheme (to prevent DC) or any other suitable encoding scheme to encode both the control data and the one or more power signals onto a single carrier signal that is transmitted to secondary auditory prosthesis 106) by way of the single wire. In some examples, the body of the patient may be used as a return path associated with the single wire. Alternatively, another wire connecting secondary auditory prosthesis 106 to primary auditory prosthesis 104 may be used as the return path.

Alternatively, control facility 304 may decouple the transmission of control data from the transmission of power signals by transmitting the control data and the one or more power signals by way of separate channels each formed by two or more wires. For example, four wires may connect secondary auditory prosthesis 106 to primary auditory prosthesis 104, as shown in FIG. 2C. Two of the wires may be configured to serve as a first channel (e.g., a differential-pair channel) by which control data is transmitted and the other two wires may be configured to serve as a second channel by which one or more power signals are transmitted. In this case, the second channel may form a charge balanced AC link of a relatively narrow bandwidth and high Q to facilitate high efficiency transmission.

In some examples, control facility 304 may receive back-telemetry data from primary auditory prosthesis 104 and/or secondary auditory prosthesis 106. For example, secondary auditory prosthesis 106 may transmit back-telemetry data to control facility 304 by way of one or more wires that connect secondary auditory prosthesis 106 to primary auditory prosthesis 104. In some examples, back-telemetry data may be transmitted by secondary auditory prosthesis 106 to control facility 304 by way of one or more wires at the same time that control data and/or one or more power signals are transmitted to secondary auditory prosthesis 106 by way of the same one or more wires. To this end, any suitable bidirectional communication protocol (e.g., a time and/or frequency multiplexed communication protocol) may be used to transmit data in either direction across the one or more wires.

Control facility 304 may be configured to generate control data and/or one or more power signals for transmission to auditory prostheses 104 and/or 106 in any suitable manner as may serve a particular implementation. For example, control facility 304 may perform one or more sound processing operations on one or more audio signals presented to an auditory prosthesis patient and generate the control data in accordance with the sound processing operations.

In some examples, control facility 304 may be configured to detect whether secondary auditory prosthesis 106 is communicatively coupled to primary auditory prosthesis 104. This may be performed in any suitable manner. If control facility 304 detects that secondary auditory prosthesis 106 is not communicatively coupled to primary auditory prosthesis 104, for example, control facility 304 may prevent all transmission of data and power signals to secondary auditory prosthesis 106. In this manner, safety of system 100 may be ensured and the risk of exposure of tissue to undesirable current may be minimized.

In some examples, control facility 304 may detect that a particular wire connecting secondary auditory prosthesis 106 to primary auditory prosthesis 104 has become broken or otherwise disabled. In response, control facility 304 may prevent additional data from being transmitted by way of the broken wire. Control facility 304 may detect that a wire has become broken in any suitable manner. For example, secondary auditory prosthesis 106 may be configured to periodically transmit test data by way of the wire to sound processor 102. If the wire becomes broken, control facility 304 may detect a failure to receive the test data and thereby determine that the wire is broken.

Control facility 304 may be configured to perform one or more fail-over operations in event of a wire breakage. For example, control facility 304 may attempt to transmit control data to secondary auditory prosthesis 106 by way of a particular wire that connects secondary auditory prosthesis 106 to primary auditory prosthesis 104. Control facility 304 may then detect a failure of secondary auditory prosthesis 106 to receive the control data. In response, control facility 304 may retransmit the control data to secondary auditory prosthesis 106 by way of a different wire that connects secondary auditory prosthesis 106 to primary auditory prosthesis 104.

Storage facility 306 may be configured to maintain control data 308 representative of one or more types of control data (e.g., stimulation parameters) that may be transmitted to primary auditory prosthesis 104 and/or secondary auditory prosthesis 106 and power data 310 associated with one or more power signals that may be transmitted to primary auditory prosthesis 104 and/or secondary auditory prosthesis 106. Storage facility 306 may be configured to maintain additional or alternative data as may serve a particular implementation.

Figure 4:
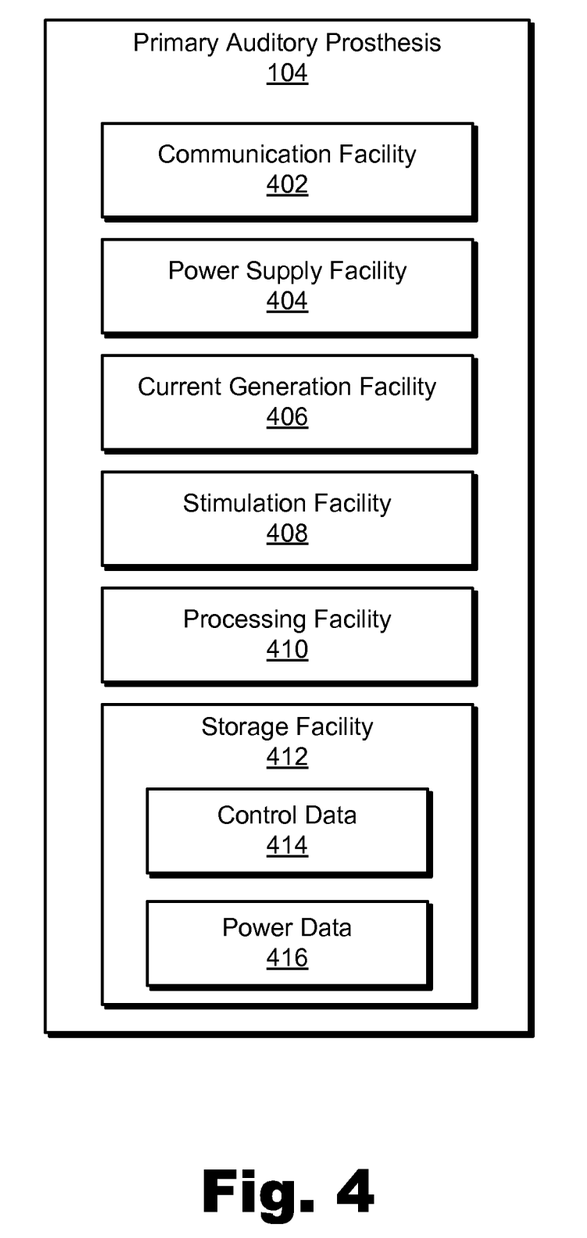
FIG. 4 illustrates exemplary components of a primary auditory prosthesis according to principles described herein.

FIG. 4 illustrates exemplary components of primary auditory prosthesis 104. As shown in FIG. 4, primary auditory prosthesis 104 may include a communication facility 402, a power supply facility 404, a current generation facility 406, a stimulation facility 408, a processing facility 410, and a storage facility 412, which may be in communication with one another using any suitable communication technologies. Each of these facilities may include any combination of hardware, software, and/or firmware as may serve a particular application. For example, one or more of facilities 402-412 may include a computing device or processor configured to perform one or more of the functions described herein. Facilities 402-412 will now be described in more detail.

Communication facility 402 may be configured to facilitate communication between primary auditory prosthesis 104 and sound processor 102. For example, communication facility 402 may include or be in communication with one or more coils configured to receive control data and/or power signals from sound processor 102 (e.g., by way of communication link 116). Communication facility 402 may additionally or alternatively be configured to transmit one or more status signals and/or other data to sound processor 102.

Communication facility 402 may be further configured to facilitate communication between primary auditory prosthesis 104 and secondary auditory prosthesis 106. For example, communication facility 402 may be implemented at least in part by a port configured to facilitate removable coupling of one or more wires connected to secondary auditory prosthesis 106.

Power supply facility 404 may be configured to provide power to various components included within primary auditory prosthesis 104. To this end, power supply facility 404 may be configured to derive power from one or more power signals received from sound processor 102.

Current generation facility 406 may be configured to generate stimulation current in accordance with control data received from sound processor 102. To this end, current generation facility 406 may include one or more current generators and/or any other circuitry configured to facilitate generation of stimulation current. For example, current generation facility 406 may include an array of independent current generators each corresponding to a distinct electrode or channel.

Stimulation facility 408 may be configured to facilitate application of the stimulation current generated by current generation facility 406 to one or more stimulation sites within the patient in accordance with the control data received from sound processor 102.

Processing facility 410 may be configured to process control data and/or power signals received from sound processor 102. For example, processing facility 410 may determine that control data received from sound processor 102 is configured to control an operation of secondary auditory prosthesis 106. This determination may be made independently or under the direction of sound processor 102. In response to the determination, processing facility 410 may transmit the control data to secondary auditory prosthesis 106 by way of one or more wires that connect secondary auditory prosthesis 106 to primary auditory prosthesis 104.

Likewise, processing facility 410 may determine that one or more power signals received from sound processor 102 are intended for secondary auditory prosthesis 106. This determination may be made independently or under the direction of sound processor 102. In response to the determination, processing facility 410 may transmit the one or more power signals to secondary auditory prosthesis 106 by way of one or more wires that connect secondary auditory prosthesis 106 to primary auditory prosthesis 104.

Storage facility 412 may be configured to maintain control data 414 and power data 416 received from sound processor 102. Storage facility 412 may be configured to maintain additional or alternative data as may serve a particular implementation.

Figure 5:
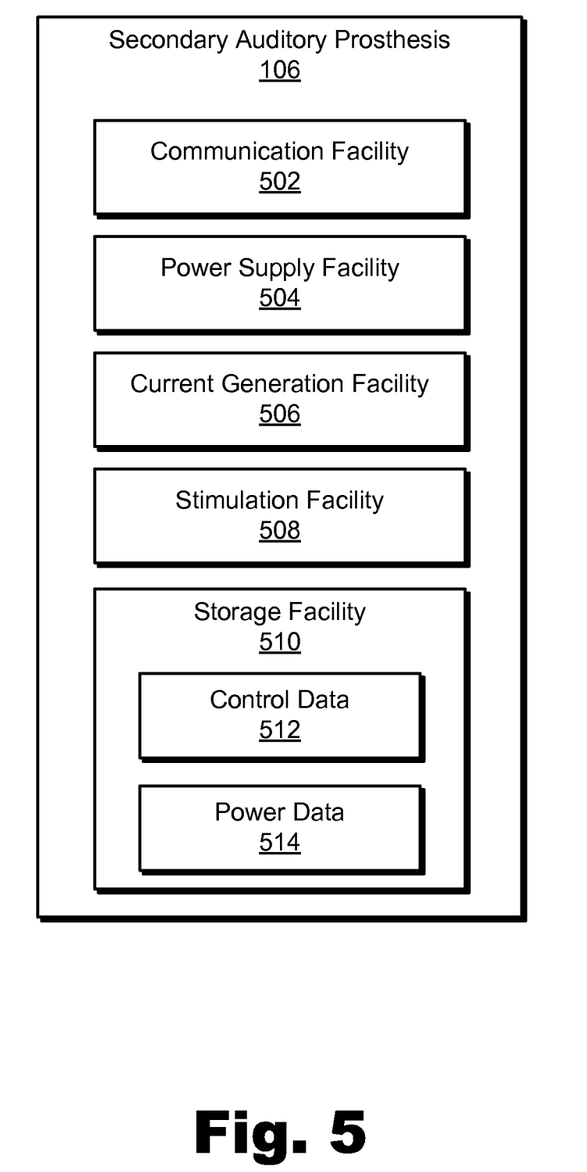
FIG. 5 illustrates exemplary components of a secondary auditory prosthesis according to principles described herein.

FIG. 5 illustrates exemplary components of secondary auditory prosthesis 106. As shown in FIG. 5, secondary auditory prosthesis 106 may include a communication facility 502, a power supply facility 504, a current generation facility 506, a stimulation facility 508, and a storage facility 514, which may be in communication with one another using any suitable communication technologies. Each of these facilities may include any combination of hardware, software, and/or firmware as may serve a particular application. For example, one or more of facilities 502-510 may include a computing device or processor configured to perform one or more of the functions described herein. Facilities 502-510 will now be described in more detail.

Communication facility 502 may be configured to facilitate communication between secondary auditory prosthesis 106 and primary auditory prosthesis 104. For example, communication facility 502 may be implemented at least in part by a port configured to facilitate connection of one or more wires (e.g., wires 202) to secondary auditory prosthesis 106.

Power supply facility 504 may be configured to provide power to various components included within secondary auditory prosthesis 106. To this end, power supply facility 504 may be configured to derive power from one or more power signals received from sound processor 102 by way of primary auditory prosthesis 104 and one or more wires.

Current generation facility 506 may be configured to generate stimulation current in accordance with control data received from sound processor 102 by way of primary auditory prosthesis 104 and one or more wires. To this end, current generation facility 506 may include one or more current generators and/or any other circuitry configured to facilitate generation of stimulation current. For example, current generation facility 506 may include an array of independent current generators each corresponding to a distinct electrode or channel.

Stimulation facility 508 may be configured to facilitate application of the stimulation current generated by current generation facility 506 to one or more stimulation sites within the patient in accordance with the control data received from sound processor 102.

Storage facility 510 may be configured to maintain control data 512 and power data 514 received from primary auditory prosthesis 104. Storage facility 510 may be configured to maintain additional or alternative data as may serve a particular implementation.

Various implementations of system 100 will now be described. It will be recognized that the various implementations of system 100 described herein are merely illustrative of the many possible implementations of system 100.

Figure 6:
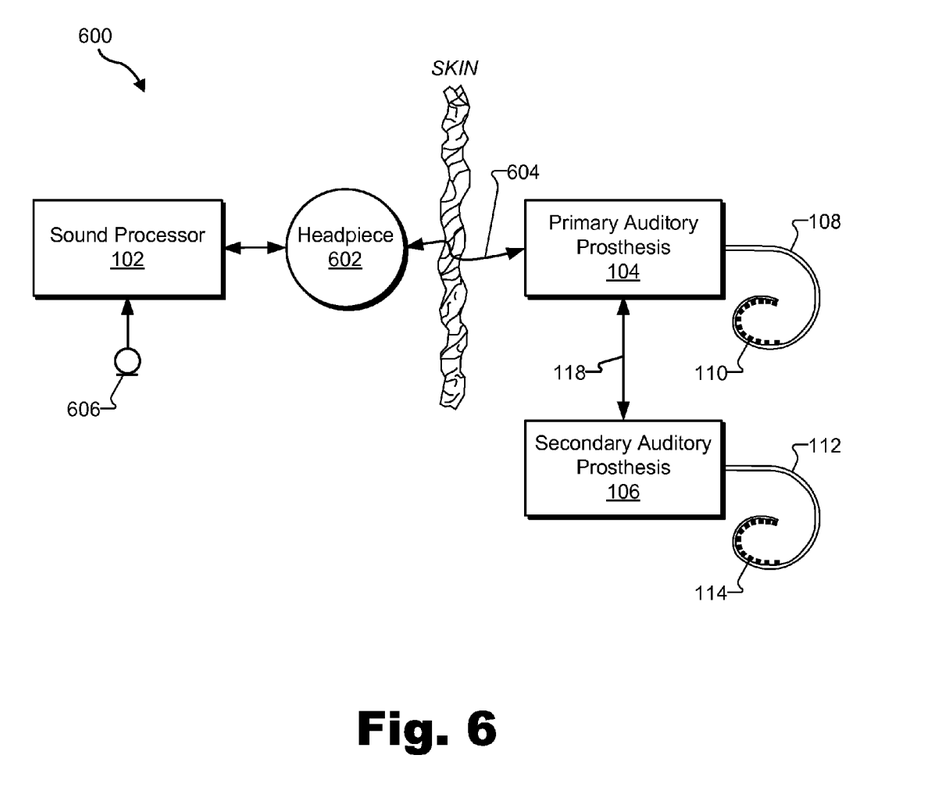
FIG. 6 illustrates an exemplary implementation of the system of FIG. 1 in which the sound processor is located external to the patient according to principles described herein.

FIG. 6 illustrates an exemplary implementation 600 of system 100 in which sound processor 102 is located external to the patient. As shown, sound processor 102 may be communicatively coupled to a headpiece 602, which may include communication component(s) (e.g., a coil) configured to facilitate wireless communication with primary auditory prosthesis 104 by way of a wireless communication link 604. In this configuration, sound processor 102 may be further coupled to a microphone 606 that may be appropriately positioned to detect audio signals presented to the patient.

Figure 7:
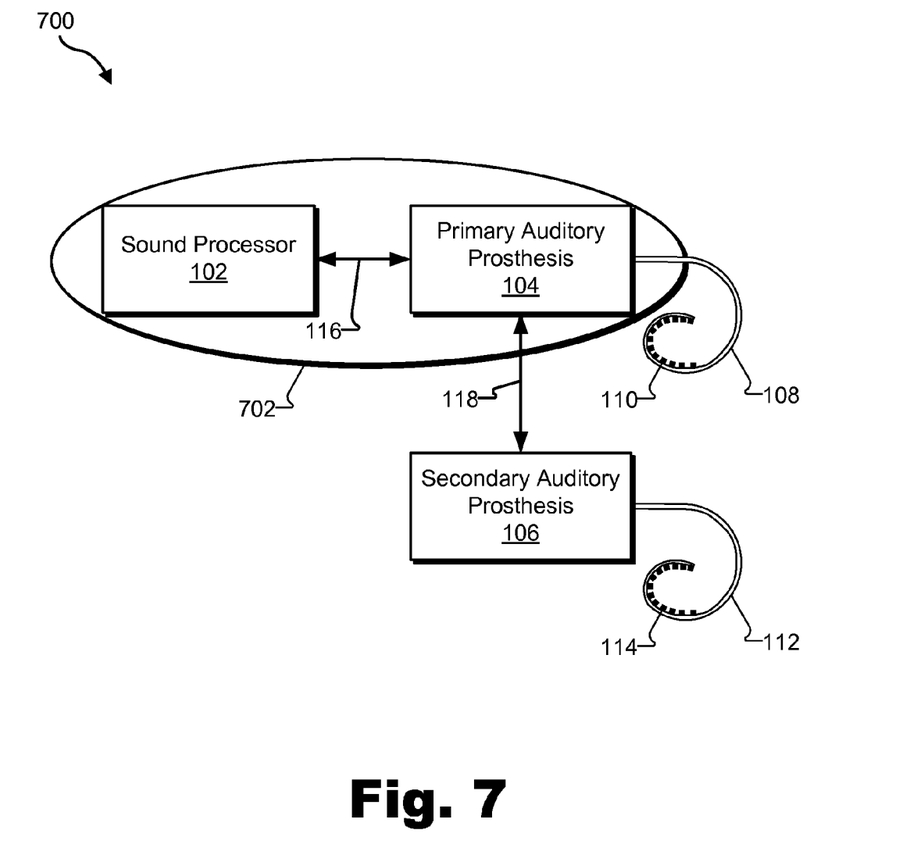
FIG. 7 illustrates another exemplary implementation of the system of FIG. 1 in which the sound processor is implanted within the patient on the same side of the head as the primary auditory prosthesis according to principles described herein.

FIG. 7 illustrates another exemplary implementation of system 100 in which sound processor 102 is implanted within the patient on the same side of the head as primary auditory prosthesis 104. As shown, sound processor 102 and primary auditory prosthesis 104 may be separate units housed within an overmold 702. By keeping sound processor 102 and primary auditory prosthesis 104 separate (as opposed to being integrated into a single unit), the overall profile (i.e., height) of the implanted components may be minimized. Overmold 702 may be made out of any suitable material as may serve a particular implementation and may include a coil (not shown) integrated therein. The coil may be used to communicate with one or more external charging devices used to recharge (i.e., provide power to) sound processor 102 and primary auditory prosthesis 104.

Figure 8:
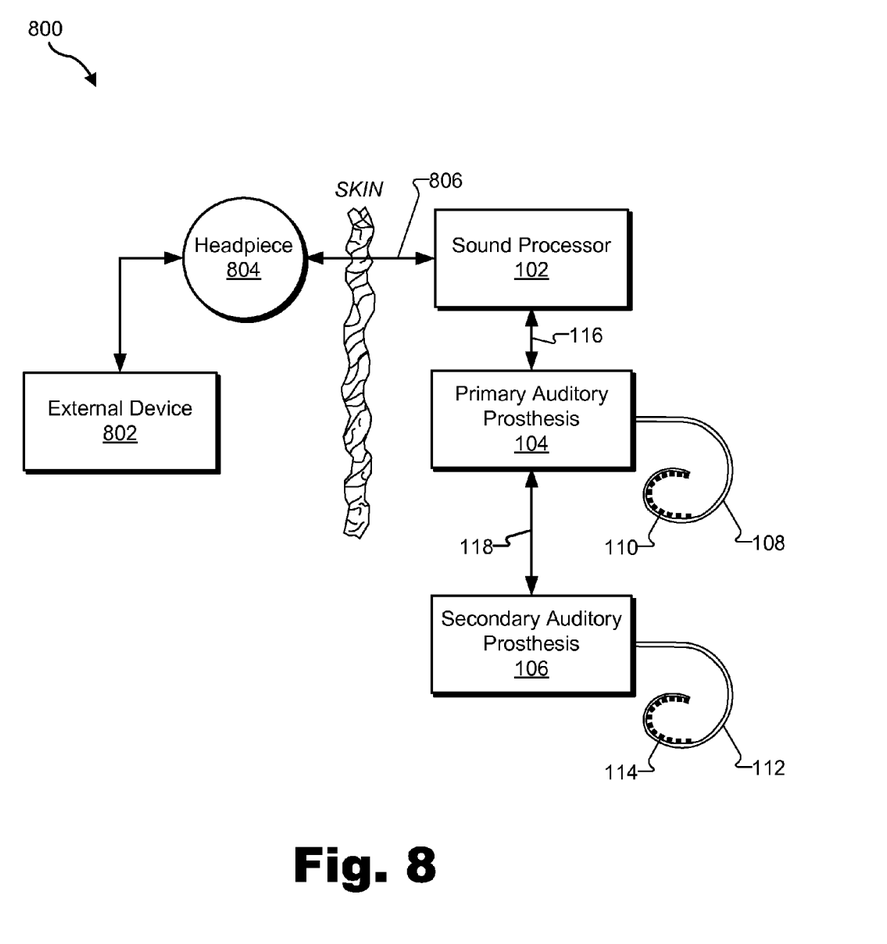
FIG. 8 shows another exemplary implementation of the system of FIG. 1 in which the sound processor is implanted within the patient according to principles described herein.

FIG. 8 shows another exemplary implementation of system 100 in which sound processor 102 is implanted within the patient. As shown, sound processor 102 may be implanted anywhere within the patient as may serve a particular implementation. For example, sound processor 102 may be implanted within the head of the patient, within the chest cavity, and/or at any other suitable location. In implementations wherein sound processor 102 is implanted within the chest cavity, sound processor 102, primary auditory prosthesis 104, and secondary auditory prosthesis 106 may be interconnected as shown in FIG. 8. Alternatively, both auditory prostheses 104 and 106 may be connected directly to sound processor 102 with one or more wires.

As shown in FIG. 8, sound processor 102 may be configured to communicate with an external device 802 (i.e., a device located external to the patient) by way of a headpiece 804. Headpiece 804 may be configured to communicate with sound processor 102 by way of a wireless communication link 806 and may include one or more interface components (e.g., transceiver components) configured to facilitate selective communicative coupling of sound processor 102 to external device 802. External device 802 may include a charging station, a fitting device, an auxiliary audio device, a microphone, and/or any other suitable external device as may serve a particular implementation.

Figure 9:
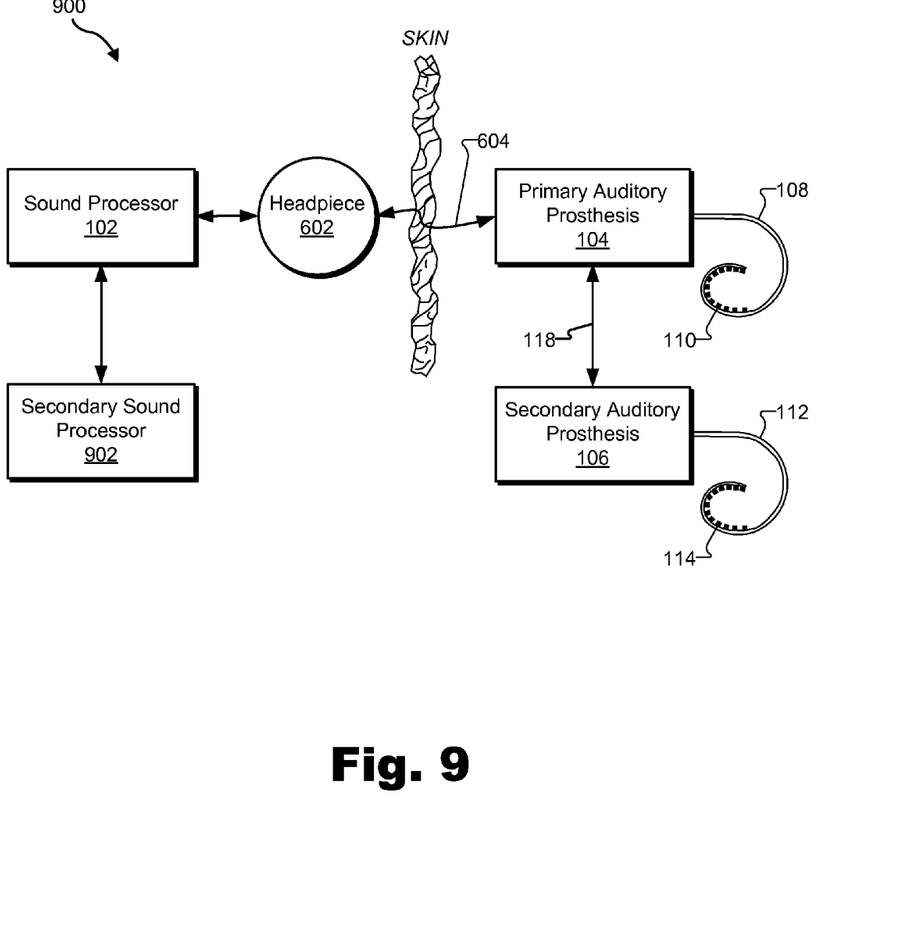
FIG. 9 shows another exemplary implementation of the system of FIG. 1 in which a secondary sound processor is communicatively coupled to the sound processor according to principles described herein.

FIG. 9 shows another exemplary implementation of system 100 in which a secondary sound processor 902 is communicatively coupled (wirelessly or wired) to sound processor 102. Secondary sound processor 902 may be worn, for example, on the same side of the head as secondary auditory prosthesis 106 and may be configured to assist sound processor 102 in processing audio signals and generating control data. For example, secondary sound processor 902 may be in communication with a microphone (not shown) located on the same side of the head as secondary auditory prosthesis 106 and thereby detect audio content presented to the patient. Data representative of the detected audio content may be transmitted to sound processor 102, which may generate and transmit control data to auditory prostheses 104 and 106.

Figure 10:
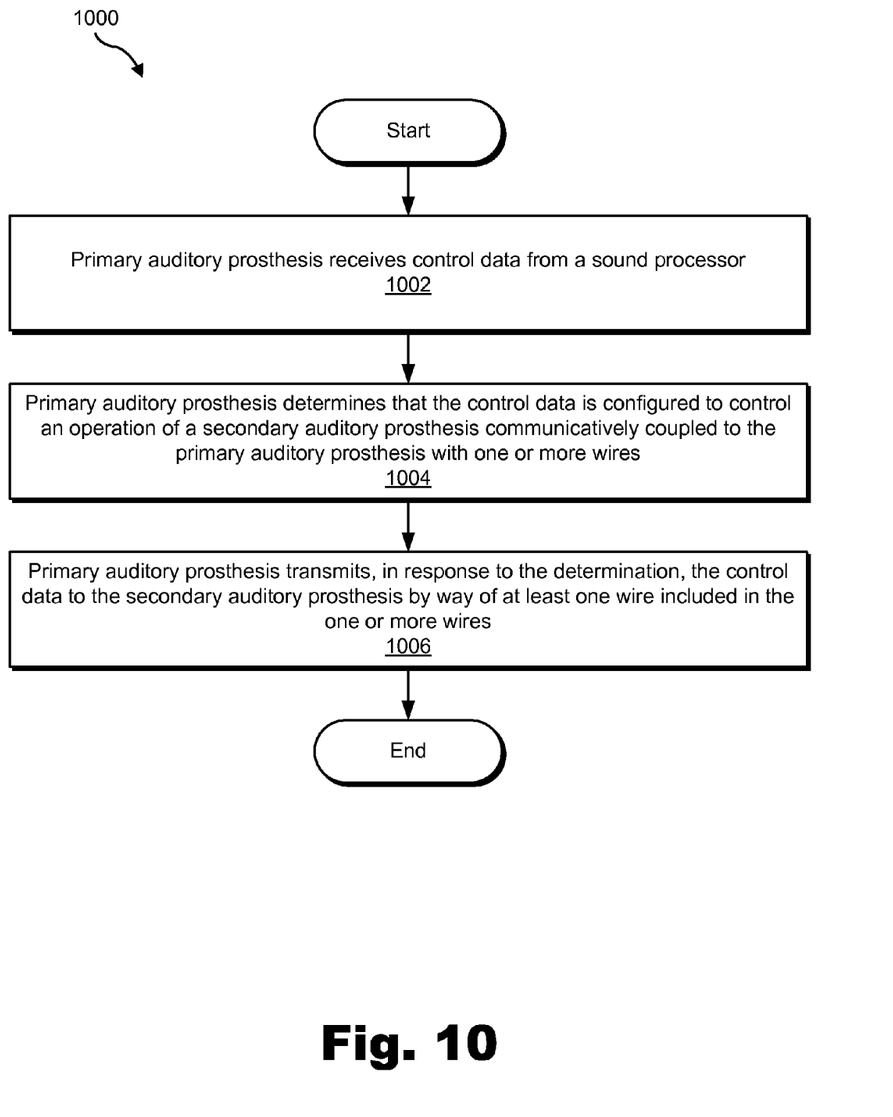
FIG. 10 illustrates an exemplary bilateral auditory prosthesis method according to principles described herein.

FIG. 10 illustrates an exemplary bilateral auditory prosthesis method 1000. While FIG. 10 illustrates exemplary steps according to one embodiment, other embodiments may omit, add to, reorder, and/or modify any of the steps shown in FIG. 10. One or more of the steps shown in FIG. 10 may be performed by any component or combination of components of primary auditory prosthesis 104.

In step 1002, a primary auditory prosthesis receives control data from a sound processor. Step 1002 may be performed in any of the ways described herein.

In step 1004, the primary auditory prosthesis determines that the control data is configured to control an operation of a secondary auditory prosthesis communicatively coupled to the primary auditory prosthesis with one or more wires. Step 1004 may be performed in any of the ways described herein.

In step 1006, the primary auditory prosthesis transmits, in response to the determination, the control data to the secondary auditory prosthesis by way of at least one wire included in the one or more wires. Step 1006 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    a primary auditory prosthesis configured to be implanted within and on a first side of a head of a patient;
    a secondary auditory prosthesis configured to be implanted within and on a second side of the head of the patient and to be communicatively coupled to the primary auditory prosthesis with one or more wires, the second side being contralateral to the first side; and
    a sound processor configured to be communicatively coupled to the primary auditory prosthesis and to control an operation of the secondary auditory prosthesis by
        performing a sound processing operation on an audio signal presented to the patient,
        generating control data in accordance with the sound processing operation, and
        transmitting the control data to the secondary auditory prosthesis by way of the primary auditory prosthesis and at least one wire included in the one or more wires, wherein the control data is configured to direct the secondary auditory prosthesis to apply electrical stimulation representative of the audio signal to one or more stimulation sites within the patient by way of one or more electrodes communicatively coupled to the secondary auditory prosthesis.

2. The system of claim 1, wherein the sound processor is configured to transmit the control data to the secondary auditory prosthesis by way of the primary auditory prosthesis and the at least one wire by transmitting the control data to the primary auditory prosthesis and directing the primary auditory prosthesis to transmit the control data to the secondary auditory prosthesis by way of the at least one wire.

3. The system of claim 1, wherein the sound processor is further configured to provide power to the secondary auditory prosthesis by transmitting one or more power signals to the secondary auditory prosthesis by way of the primary auditory prosthesis and at least one wire included in the one or more wires.

4. The system of claim 3, wherein the sound processor is configured to transmit both the control data and the one or more power signals to the secondary auditory prosthesis by way of the primary auditory prosthesis and a single wire included in the one or more wires.

5. The system of claim 4, wherein the sound processor is configured to use a charge balanced data encoding scheme to transmit one or both the control data and the one or more power signals to the secondary auditory prosthesis by way of the primary auditory prosthesis and the single wire and to use a body of the patient as a return path associated with single wire.

6. The system of claim 4, wherein the sound processor is configured to use a charge balanced data encoding scheme to transmit both the control data and the one or more power signals to the secondary auditory prosthesis by way of the primary auditory prosthesis and the single wire and to use another wire included in the one or more wires as a return path associated with the single wire.

7. The system of claim 3, wherein the sound processor is configured to:
transmit the control data to the secondary auditory prosthesis by way of a first channel comprising two wires included in the one or more wires; and
transmit the one or more power signals to the secondary auditory prosthesis by way of a second channel comprising another two wires included in the one or more wires, the second channel being decoupled from the first channel.

8. The system of claim 1, wherein the one or more wires comprises a first set of one or more wires and a second set of one or more wires that is redundant to the first set of one or more wires.

9. The system of claim 8, wherein the sound processor is configured to transmit the control data to the secondary auditory prosthesis by:
attempting to transmit the control data to the secondary auditory prosthesis by way of at least one wire included in the first set of one or more wires;
detecting a failure of the secondary auditory prosthesis to receive the control data; and
transmitting, in response to the detection, the control data to the secondary auditory prosthesis by way of at least one wire included in the second set of one or more wires.

10. The system of claim 1, wherein the sound processor is further configured to control an operation of the primary auditory prosthesis by transmitting additional control data to the primary auditory prosthesis.

11. The system of claim 10, wherein the sound processor is configured to concurrently transmit the control data to the secondary auditory prosthesis and the additional control data to the primary auditory prosthesis.

12. The system of claim 1, wherein the sound processor is configured to be located external to the patient.

13. The system of claim 1, wherein the sound processor is configured to be at least partially implanted in the patient.

14. The system of claim 13, wherein the sound processor and the primary auditory prosthesis are separate units, and wherein the system further comprises an overmold configured to house both the sound processor and the primary sound processor.

15. The system of claim 13, further comprising a headpiece configured to be located external to the patient and to be communicatively coupled to the sound processor, the headpiece comprising one or more interface components configured to facilitate selective communicative coupling of the sound processor to one or more external devices.

16. The system of claim 1, wherein at least one of the sound processor and the primary auditory prosthesis is further configured to:
detect that at least one of the one or more wires is broken; and
prevent additional data from being transmitted by way of the at least one broken wire.

17. An auditory prosthesis implanted within a patient and comprising:
a communication facility that receives control data from a sound processor that generates the control data by performing a sound processing operation on an audio signal presented to the patient; and
a processing facility communicatively coupled to the communication facility and that
determines that the control data is configured to control an operation of a secondary auditory prosthesis implanted within the patient and communicatively coupled to the auditory prosthesis with one or more wires tunneled across the head of the patient, and
transmits, in response to the determination, the control data to the secondary auditory prosthesis by way of at least one wire included in the one or more wires tunneled across the head of the patient, wherein the control data is configured to direct the secondary sound processor to apply electrical stimulation representative of the audio signal to one or more stimulation sites within the patient by way of one or more electrodes communicatively coupled to the secondary auditory prosthesis.

18. The auditory prosthesis of claim 17, wherein:
the receiving facility is further configured to receive one or more power signals from the sound processor;
the processing facility is further configured to determine that the one or more power signals are intended for the secondary auditory prosthesis; and
the interface facility is further configured to transmit, in response to the determination that the one or more power signals are intended for the secondary auditory prosthesis, the one or more power signals to the secondary auditory prosthesis by way of at least one wire included in the one or more wires.

19. A method comprising:
receiving, by a primary auditory prosthesis implanted within a patient, control data from a sound processor that generates the control data by performing a sound processing operation on an audio signal presented to the patient;
determining, by the primary auditory prosthesis, that the control data is configured to control an operation of a secondary auditory prosthesis implanted within the patient and communicatively coupled to the primary auditory prosthesis with one or more wires tunneled across the head of the patient; and
transmitting, by the primary auditory prosthesis in response to the determination, the control data to the secondary auditory prosthesis by way of at least one wire included in the one or more wires tunneled across the head of the patient, wherein the control data is configured to direct the secondary sound processor to apply electrical stimulation representative of the audio signal to one or more stimulation sites within the patient by way of one or more electrodes communicatively coupled to the secondary auditory prosthesis.

20. The system of claim 1, wherein the one or more wires are tunneled across the head of the patient.

\* \* \* \* \*